United States Patent [19]

Haaga

[11] Patent Number: 5,447,502
[45] Date of Patent: Sep. 5, 1995

[54] SHEATH FOR WOUND CLOSURE CAUSED BY A MEDICAL TUBULAR DEVICE

[76] Inventor: John R. Haaga, 4309 N. Hilltop, Chagrin Falls, Ohio 44022

[21] Appl. No.: 219,169

[22] Filed: Mar. 28, 1994

Related U.S. Application Data

[60] Continuation of Ser. No. 84,135, Jul. 1, 1993, Pat. No. 5,330,445, which is a division of Ser. No. 896,588, Jun. 10, 1992, Pat. No. 5,254,105, which is a continuation-in-part of Ser. No. 787,518, Nov. 4, 1991, Pat. No. 5,195,988, which is a division of Ser. No. 514,769, Apr. 26, 1990, Pat. No. 5,080,655, which is a division of Ser. No. 288,858, Dec. 23, 1988, Pat. No. 4,936,835, which is a continuation-in-part of Ser. No. 199,130, May 26, 1988, Pat. No. 4,838,280.

[51] Int. Cl.$^6$ .............................. A61M 5/32
[52] U.S. Cl. ................................. 604/265
[58] Field of Search ............... 128/642, 754; 604/265, 604/280; 606/109, 192

[56] References Cited

U.S. PATENT DOCUMENTS

| | | | |
|---|---|---|---|
| 2,603,217 | 7/1952 | McShirley | 128/239 |
| 2,691,373 | 10/1954 | Bried | 128/239 |
| 2,814,296 | 11/1957 | Everett | 128/339 |
| 3,106,483 | 10/1963 | Kline et al. | 117/622 |
| 3,358,684 | 12/1967 | Marshall | 128/2144 |
| 3,396,727 | 8/1968 | Mount | 128/349 |
| 3,530,860 | 9/1970 | Majoros | 128/305 |
| 3,736,939 | 6/1973 | Taylor | 128/349 B |
| 3,888,258 | 6/1975 | Akiyama | 128/305 |
| 4,306,563 | 12/1981 | Iwatschenko | 128/349 B |
| 4,317,455 | 3/1982 | Robinson | 128/214 |
| 4,390,018 | 6/1983 | Zukowski | 128/303 |
| 4,396,021 | 8/1983 | Baumgartner | 128/754 |
| 4,564,361 | 1/1986 | Akiyama | 604/265 |
| 4,646,739 | 3/1987 | Doyle | 606/192 |
| 4,650,488 | 3/1987 | Bays et al. | 623/12 |
| 4,710,181 | 12/1987 | Fugua | 604/280 |
| 4,774,091 | 9/1988 | Yamahira | 424/426 |
| 4,774,364 | 9/1988 | Kensey | 128/334 |
| 4,827,940 | 5/1989 | Mayer et al. | 128/642 |
| 4,890,612 | 1/1990 | Kensey | 606/213 |
| 5,108,421 | 4/1992 | Fowler | 606/213 |
| 5,222,974 | 6/1993 | Kensey | 606/313 |
| 5,282,827 | 2/1994 | Kensey | 606/215 |

FOREIGN PATENT DOCUMENTS

| | | |
|---|---|---|
| 0019104 | 4/1980 | European Pat. Off. . |
| 0139091 | 7/1984 | European Pat. Off. . |
| 0482350 | 9/1991 | European Pat. Off. . |
| 862592 | 11/1987 | Germany . |
| 3632197 | 3/1988 | Germany . |

OTHER PUBLICATIONS

Gazelle et al., Radiology; 175:671–674; Jun., 1990.
Rosen, Diagnostic Angiography, 1986.
Takayasu et al., Jpn J. Clin. Oncol., 18:227–230, 1988.

*Primary Examiner*—Max Hindenburg
*Attorney, Agent, or Firm*—Vickers, Daniels & Young

[57] ABSTRACT

A tubular sheath is disclosed which is slidably disposed over a tubular medical device which tubular medical device is positioned at a body tissue access site. The sheath is deposited within a patient to assist in sealing the incision caused by the tubular medical device and inhibit internal and external bleeding. The sheath includes a generally rigid outer coating and an absorbable and expandable inner core, which when positioned, in situ, at the accessed opening of the patient's body part can function as a vascular plug.

28 Claims, 2 Drawing Sheets

SHEATH FOR WOUND CLOSURE CAUSED BY A MEDICAL TUBULAR DEVICE

This application is a continuation of Ser. No. 08/084,135 filed Jul. 1, 1993 now U.S. Pat. No. 5,330,445 which is a division of Ser. No. 07/896,588 filed Jun. 10, 1992 now U.S. Pat. No. 5,254,105 which is a continuation-in-part of Ser. No. 07/787,518 filed Nov. 04, 1991 now U.S. Pat. No. 5,195,988 which is a division of Ser. No. 07/514,769 filed Apr. 26, 1990 now U.S. Pat. No. 5,080,655 which is a division of Ser. No. 07/288,858 filed Dec. 23, 1988 now U.S. Pat. No. 4,936,835 which is a continuation-in-part of Ser. No. 07/199,130 filed May 26, 1988 now U.S. Pat. No. 4,838,280.

This invention relates generally to a device for use with or in combination with a wide range of medical instruments which device is left in situ within the patient, after and/or during use of the medical instrument, for purposes of avoiding or preventing hemorrhagic complications arising from the wound caused by the instrument.

The invention is particularly applicable to a cardiovascular device and process in the general form of a hollow tubular sheath deposited in the patient's tissue area to inhibit bleeding and seal or plug the access site and will be described with particular reference thereto. However, it is to be understood by those skilled in the art that the invention has broader medical applications and is not to be limited to its use as a cardiovascular plug.

INCORPORATION BY REFERENCE

My prior applications identified above, and specifically my prior U.S. Pat. Nos. 4,838,280 dated Jun. 13, 1989, and 4,936,835 dated Jun. 26, 1990 are incorporated by reference herein and made a part hereof so that the specifications hereof need not describe the invention to that detailed extent which the invention would otherwise be described. In addition, U.S. Pat. Nos. 3,358,684 dated Dec. 19, 1987, and 3,106,483 dated are also incorporated by reference herein so that the specifications need not disclose in detail information known in the art.

BACKGROUND

There are numerous medical procedures and devices in use today in which a medical device, generally tubular, such as a laparoscope, trocar, electrode, probe, introducer, or the like is inserted into the abdomen, chest, or body parts of a patient for performing some procedure or inspection after which tile device is withdrawn. When the device is inserted, a wound results and hemorrhagic complications arise during the insertion and/or removal of the device. Until my invention, there was no known device which addressed the hemorrhagic complications arising from the wound. If complications arose, the wound was treated in accordance with sound medical practice employing conventional techniques.

Within the prior art, the use of gelatin as a substance for making medication capsules for internal use and adapted to be absorbed by enzyme action or other physiological processes within the body is well known. Also, the use of gelatin material for various surgical techniques has been well documented. In particular, the use of a gelatin material in a "sponge" form or as a foam is commercially available from the Upjohn Company under the trademark "Gelfoam". Gelfoam with and without thrombin, a protein which is active at the last stage of clot formation and functions to change fibrinogen to fibrin, has been used in surgery in virtually all organ systems including prostrate, brain, musculoskeletal, vascular graphs and other areas without adverse complications. The use of gelatin as a coating for a fabric, blood-vessel graft is disclosed in U.S. Pat. No. 3,106,483 to Kline et al dated Oct. 8, 1963, incorporated herein by reference.

The use of hardened gelatin as forming a part of a surgical instrument is disclosed in U.S. Pat. No. 3,358,684 to Marshall dated Dec. 19, 1967, incorporated by reference herein. In Marshall, the distal cutting edge of a cannula which is used as a parenteral injection device is formed from a thiolated gelatin material. Specifically, the gelatin distal tip punctures a vein, and eventually dissolves, leaving the proximal portion of the cannula within the vein for administrating parenteral solutions. The cannula can be thus left in situ without vein damage which would otherwise arise from the presence of a sharp needle or the removal of the sharp needle from the vein. In this sense, the prior art recognizes that it is known to use gelatin as a surgical instrument which can be dissolved at the insertion site.

SUMMARY OF THE INVENTION

A) Invention as disclosed in my prior application(s).

In my '280 patent, I disclosed a hemostatic sheath made of a bioabsorbable material, such as gelatin, which was slidably disposed over a biopsy needle. The needle caused a wound and the gelatin sheath plugged the wound after the needle was removed to enhance blood clotting and avoid hemorrhagic complications. The gelatin, being bioabsorbable, eventually dissolves, thus eliminating any need for post surgical treatment of the wound.

In my '835 continuation-in-part patent, I disclosed several variations and extensions of my sheath. Insofar as this invention is concerned, I disclosed a non-bioabsorbable sheath for use with a needle in which the sheath was dimensionally sized to compress the wound caused by the needle puncture which compression of the patient's tissue minimized bleeding. Optionally the sheath was coated with thrombin, a substance recognized for its blood clotting abilities. Still more specifically, it was recognized in my '835 patent that the gelatin sheath could also be sized to achieve compression of the tissue wound and that gelatin, in its initial hardened state, could be easily inserted into the site. The non-bioabsorbable sheath embodiment, however, permits access to the puncture site for subsequent insertion of medical devices through the sheath.

B) Preferred embodiment of invention.

It is a principal object of the present invention to provide a universal sheath applicable to a wide variety of tubular medical instruments or devices which cause a puncture in the patient's abdomen, chest, body part, etc. (or which is used with a tubular device after the puncture is caused) to minimize bleeding or hemorrhagic complications from the wound caused by the device.

This object, along with other features of the invention, is achieved in the broad sense of the invention, by a tubular medical device, such as a medical instrument, which device is inserted through the skin of the patient and at least into the patient's subcutaneous tissue, and to which a hollow tubular sheath is slidably disposed on said tubular device. A pusher mechanism associated with the medical device is used for depositing the sheath in situ at the wound for minimizing hemorrhagic complications arising from the wound. The device could be a laparascope, a trocar, an electrode, a probe, a biopsy needle, an introducer, or the like. The device need not cause the puncture in the body tissue. Another instrument could cause the puncture and the hemostatic sheath slidably mounted on a tubular introducer which, when removed, leaves the sheath as an in situ plug. The sheath could be positioned in situ either when the medical device is in use or placed in situ at the accessed tissue opening while the medical instrument or the device is removed.

In accordance with a more specific feature of the invention, the tubular medical device is used to access an opening formed in a body part such as a blood vessel, abdomen, kidney, etc., and the sheath is positioned, in situ, at accessed opening in the body part to plug or seal the opening from body fluid leakage while also preventing bleeding from the subcutaneous tissue adjacent the body part. The wound thus caused in the patient is treated by positioning the sheath of the invention at tile tissue of the body part where the body part has been accessed by the medical device.

In accordance with a specific important feature of the insertion, the outside diameter or size of the tubular sheath is sized larger than the opening at which the tissue has been accessed so that the wound is compressed to minimize bleeding.

In accordance with another feature of the invention, the sheath can be either bioabsorbable ( for reasons discussed below) or non-absorbable and made from common materials tolerated by tissue such as collagen,-gelatin, cellulose, body tolerant polymers, and other materials. In all instances, the sheath has an outer shell or casing in its initial state which becomes slippery when in contact with body fluids, such as blood, to permit the sheath to be readily inserted into the access opening.

In accordance with yet another aspect of the invention, the tubular sheath is constructed of an absorbent material with an outer casing or alternatively, an outer coating which is relatively hard in its initial dry state whereby the absorbent material, upon exposure to body fluids, dimensionally swells to occlude the central opening of the sheath and plug the tissue access site. The absorbent material can be either bioabsorbable or non-bioabsorbable depending on the application. Preferably the outer coating (or outer casing) is bioabsorbable (such as hardened gelatin) to permit the sheath to be easily positioned at the access site which coating readily dissolves to permit radially-outward expansion of the absorbent material further compressing the tissue access site and minimizing bleeding. Thus, in accordance with a still further specific feature of the invention, the thickness of the outer coating is, depending on the particular medical application, predetermined so that the absorbent material dimensionally expands radially-inwardly to occlude the opening before tile outer coating is bioabsorbed and expands radially-outwardly, Still yet another important aspect of tile invention is the formation of the tubular sheath with a soft, sticky distal axial end portion such as that which can be formed from soft collagen and a rigid, proximal axial end portion such as that achieved by an outer coating or an outer casing of hardened gelatin whereby the accessed opening formed in a blood vessel such as an artery is plugged by the distal end of the sheath conforming to the shape of the wall of the vessel when the sheath is pushed against the blood vessel. When the sheath is pushed against the vessel wall, the absorbent material expands to occlude the central opening in the sheath as noted above to seal the vessel, body part, etc.

In accordance with another feature of the invention, the tubular sheath is slit longitudinally from its distal axial end to its proximal axial end whereby the sheath can be stretched or radially expanded and applied to the tubular medical instrument or device after the instrument or device has been inserted into the patient. In this manner, the sheath is not contaminated prior to insertion. That is, some medical treatments take several hours or more to complete. During this time, the sheath could otherwise become contaminated by body fluids from the patient escaping the skin surface area and spattering into the sheath, causing a premature expansion of the absorbable sheath material and/or dissolving of the outer coating adversely affecting placement of the sheath at the tissue access site.

In accordance with still another aspect of the invention, the hemostatic sheath contains a blood clotting chemical, typically the enzyme thrombin, to accelerate blood clotting about the blood vessel wall to help reduce internal bleeding and minimize complications resulting from such bleeding.

One of the objects of the present invention is to provide a hemostatic sheath having a generally rigid outer casing and an absorbable inner core which can be deposited on a blood vessel wall to inhibit and prevent blood from escaping from the blood vessel.

Still another object of the invention is to provide a hemostatic sheath which can be applied to a medical device after the medical device has been inserted into the tissue area for preventing bleeding from the wound caused by the medical device.

Yet still a further object of the invention is to provide a hemostatic sheath with a sticky tip which readily attaches to the blood vessel wall or the tissue of the body part which has been accessed by a tubular medical device to prevent loss of body fluid from the accessed site.

Another object of the invention is to provide a sheath which contains an expandable, highly absorbable inner core which permits the sheath to plug the accessed site of a body part.

Yet another object of the present invention is to provide a sheath with a generally rigid outer core which becomes slippery when in contact with fluids to permit easy in situ application of the sheath.

Yet still another object of the present invention is to provide a sheath with a bioabsorbable or non-bioabsorbable outer shell or coating and a bioabsorbable or non-bioabsorbable inner core to prevent hemorrhagic complications from a wound to avoid post surgical treatment of the wound.

Another object of the invention is to provide an in situ sheath which in addition to preventing bleeding at the site also seals or plugs the tissue access opening.

Still another object of the invention is to provide a process for applying a sheath in situ to prevent hemorrhagic complications arising from a wound generally, and more specifically bleeding from the subcutaneous tissue and still more specifically bleeding from the subcutaneous tissue and loss of body fluid (including blood) arising from the opening formed in the body part.

A still further object of the invention is to provide an in situ vascular plug o minimize bleeding from a puncture or a tissue access opening in a body part no matter how formed.

Still yet another object of the invention is to provide a sheath in combination with a tubular pushing device to permit universal application of the sheath to the tissue of a body access site for a wide variety of medical instruments and/or introducers for preventing bleeding of the wound and thus obviate post strgical treatment of the wound.

Still another object is to provide a sheath containing blood clotting enzymes to accelerate the clotting around the sheath to minimize bleeding complications.

Further objects anti advantages of the invention will become apparent to those skilled in the art from reading and understanding the following detailed description of various embodiments of the invention.

BRIEF DESCRIPTION OF THE DRAWINGS

Reference may now be had to the drawings, which illustrate various embodiments that the invention may take in physical form and in certain parts and arrangement of parts wherein.

DETAILED DESCRIPTION OF THE INVENTION

Figure 1:
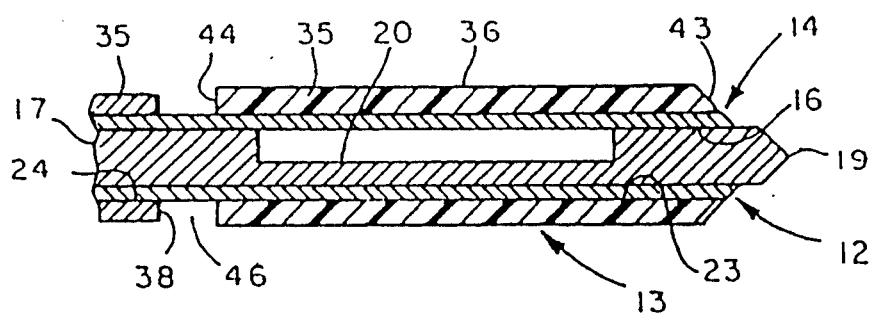
FIG. 1 is a cross-sectional view in section of the distal portion of a needle equipped with the sheath of the present invention and is the same view as that shown in FIG. 5 of my '280 patent and FIG. 8 of my '835 patent.
Figure 2:
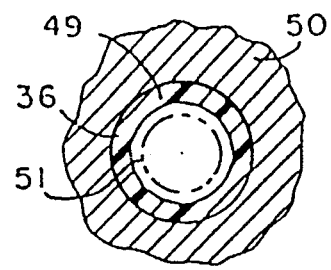
FIG. 2 is a cross-sectional view of the invention shown in an in situ position within the tissue of the patient and is the same view as that shown in FIG. 6 of my '280 patent and FIG. 9 of my '835 patent.

Referring now to the drawings wherein the showings are for the purpose of illustrating preferred embodiments of the invention only and not for the purpose of limiting the same, reference is first had to FIGS. 1 and 2, which as noted above, correspond respectively to FIGS. 5 and 6 of my '280 patent. Because my prior patents, including the drawings, are incorporated reference in specifications hereof, reference numerals for FIGS. 1 and 2 are identical to and indicate the same parts, surfaces, etc., which have been described in my prior patents. Reference to the specifications of my prior patents should be had for a more detailed explanation of the functioning of the device than that disclosed herein. In this application, reference numeral 36 in FIGS. 1 and 2 designates a removable hemostatic sheath which has a low co-efficient of friction and may be either bioabsorbable or non-bioabsorbable in nature.

As discussed in my prior patents, and as shown in FIG. 2, cutting cannula 12 leaves a generally cylindrical void defined by tissue margin 51 (initially shown as the dot-dash line) and when hemostatic sheath 36 is inserted into the void, the margin is expanded to a cylindrical edge shown as 49 and the tissue surrounding the void is compressed. I have discovered that compression of the tissue by means of hemostatic sheath 36 is sufficient to avoid hemorrhaging complications and that a bioabsorbable sheath, while preferred, is not necessary for all applications to prevent hemorrhaging. That is, sheath 36 can be non-bioabsorbable. Optionally, the non-bioabsorbable sheath could be coated with thrombin.

Figure 3:
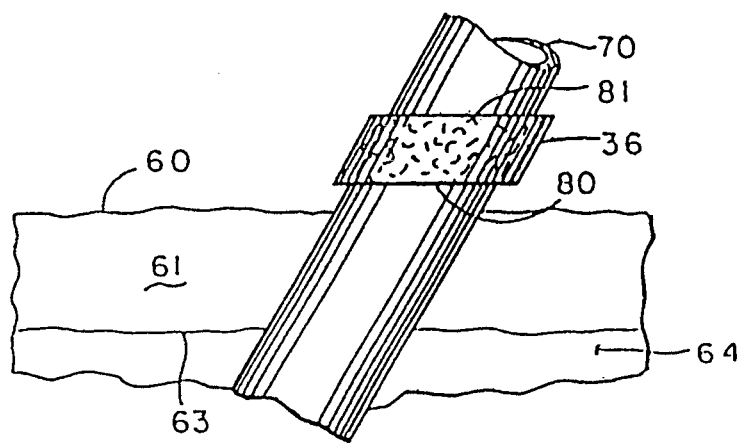
FIG. 3 is a schematic elevation view showing a medical instrument or introducer inserted into a patient with the sheath of the present invention applied thereto.
Figure 4:
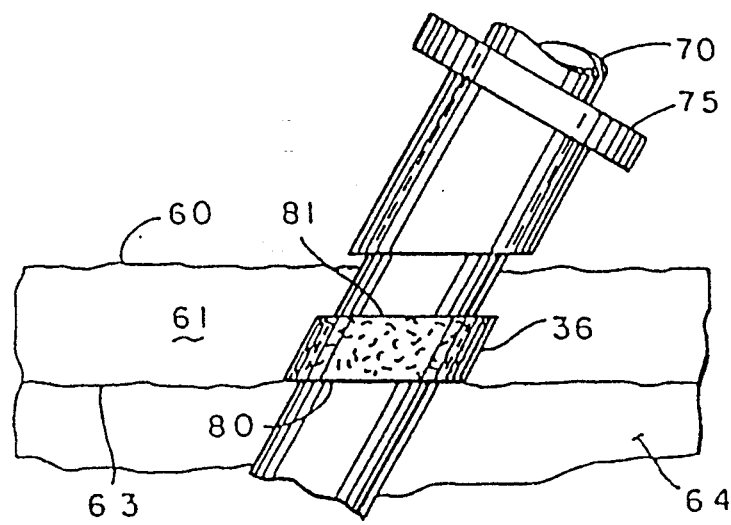
FIG. 4 is a schematic elevation view similar to FIG. 3, showing the position of the sheath within the wound and the pusher mechanism slightly retracted.
Figure 5:
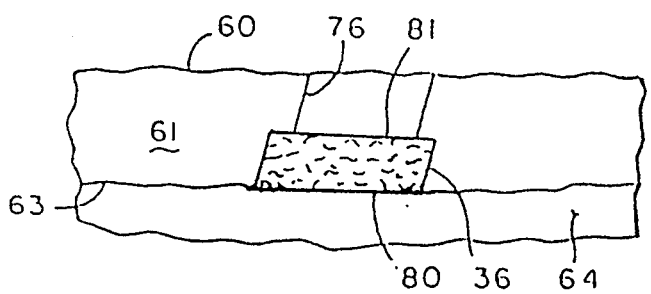
FIG. 5 is a schematic elevation view similar to FIGS. 3 and 4 with the instrument or introducer removed and is similar to FIG. 2.
Figure 6:
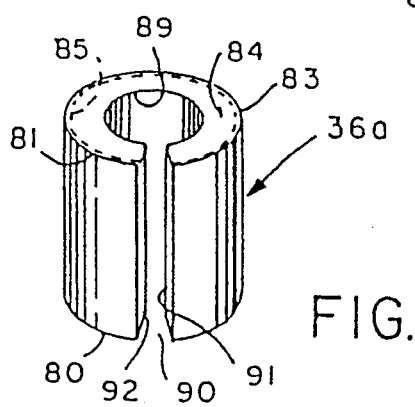
FIG. 6 is a schematic, perspective view of a modified form which the sheath of my invention can take.

The invention in its broad concept is illustrated in FIGS. 3, 4, and 5. There are countless applications of sheath 36 in the medical field and by this specification I will use certain terminology, not only in the specifications but also in the claims, to describe the invention. Accordingly, "body" means and includes all ducts, organs, body parts, as well as the vasculature. "Tissue of the body" means the tissue forming the outer surface of the body and can include as well, the tissue surrounding the body. "Access" is the opening, no matter how formed, in the tissue of the body and for vasculature applications includes trancutaneous access, as well as other types of access such as external access or extracorporeal access. Thus, use of sheath 36 at the site "where the body tissue has been accessed" means the use of sheath 36 at the site of the blood vessel or body organ and not just superficially at the skin level. Finally, "tubular medical device" includes not only medical instrument such a needles capable of puncture to gain access to the body, but also other devices capable of gaining access to the body such as a catheter, cannula, tube, introducer, and access devices.

With these definitions in mind, FIGS. 3, 4, and 5 show schematically, the patients skin 60, the subcutaneous tissue 61 lying beneath the skin, a membrane or body tissue 63 (such as the peritoneum) lining a body part 64 (such as the abdomen for the peritoneum) which body part 64 is to be accessed. (The description is generic. For cardiovascular applications, as discussed hereafter, membrane 63 is the blood vessel wall and body part 64 is the blood vessel.) Access to body part 64 may be lad by any tubular medical device 70 which is generally cylindrical. For example, medical device could be, depending on the medical procedure performed, a laparoscope, a trocar, an electrode, a probe, an introducer, or the like. As shown in FIG. 3, sheath 36 is slidably disposed on tubular medical device 70 external to the patient while medical device 70 is used to perform the desired medical procedure. When the procedure is completed, a pusher mechanism or means (i.e., plunger) 75 engages or contacts the proximal end 80 of sheath 36 and slides sheath 36 along tubular medical device 70 until membrane 63 (i.e., the peritoneum for FIGS. 3–5 under discussion) is contacted by the distal end 81 of sheath 36. In the drawings, plunger 75 is simply a hand operated tubular member slidably disposed over tubular medical device 70. Other arrangements will inherently or obviously suggest themselves to those skilled in the art depending on the nature, function, and structure of tubular medical device 70, which devices will permit accurate positioning of sheath 36 at the site where the body tissue as been accessed. FIG. 4 thus shows sheath 36 positioned in wound 76 by plunger 75 with plunger 75 being withdrawn from tubular medical device 70 and FIG. 5 shows wound 76 with sheath 36 positioned therein at the in situ position described with tubular medical device 70 withdrawn. It should be obvious that the invention does not require precise positioning of sheath 36 by plunger 75. Because of the characteristics of sheath 36, sheath 36 can be precisely positioned in situ by the surgeon after plunger 75 and tubular medical device 70 is withdrawn. In fact, this is preferred for many procedures. In accordance with the broad concept of the invention as illustrated in FIGS. 3, 4, and 5, the material for sheath 36 could be bioabsorbable or non-bioabsorbable material and common materials for sheath 36 would include collagen, gelatin, cellulose, absorbable polymers and the like.

The configuration of sheath 36 as thus far described is that of a solid hollow cylinder. An alternative configuration is shown for sheath 36a of FIG. 6 and another configuration is shown for sheath 36b of FIG. 7. For purposes of the present invention, all three sheath forms can be viewed as having an outer hardened, rigid, or form maintaining coating or casing 83 surrounding an inner softer core 84. The margin for inner core 84 is diagrammatically illustrated by the broken line identified as reference numeral 85 shown for sheath 36a in FIG. 6.

Outer coating 83 is comprised of a substance which generally maintains its form when being inserted into the patient. Outer coating 83 may be bioabsorbable, non-bioabsorbable, or semi-bioabsorbable. Typically outer coating 83 is composed of a gelatin compound. Gelatin forms a relatively rigid outer shell structure which maintains its form during the insertion procedure However, outer coating 83 may consist of collagen, cellulose, absorbable polymers, gelatin and combinations thereof. (Those skilled in the art will recognize that gelatin is a derivative of collagen. Thus in my prior applications, I disclosed collagen albeit in its gelatin form. In this specification, collagen is mentioned separately from gelatin, not in the sense of the two materials being different but in the sense that "collagen" is used to indicate a material softer than gelatin, and further it is recognized that there are varying degrees of sotfness for collagen.) Outer coating 83 is preferably a bioabsorbable material which dissolves within the patient's body. Outer coating 83 may also be composed of a substance that becomes slick upon contact with body fluids so as to allow sheath 36 to be easily inserted to the body tissue access site (i.e., membrane 63, blood vessel wall) without damaging the surrounding tissue during insertion. The slick outer coating 83 of sheath 36 acts as a lubricant to sheath 36 as it is being inserted. Normally the slick surface results from the outer coating 83 dissolving in the presence of the body fluid. Bioabsorbable materials, such as gelatin or gelatin compounds, form a very slippery surface when in contact with blood. Thus outer coating 83, depending on the application, is sized to have various thickness. The thickness of outer coating 83 depends on where sheath 12 is being applied in the body of the patient and the distance the sheath has to travel within the body to reach the desired tissue access site. If outer coating 83 of sheath 36 is composed of a bioabsorbable substance such as gelatin, outer coating 83 will be absorbed into the surrounding tissue as it is being inserted through the body, causing the thickness of outer coating 36 to decrease. Therefore, outer coating 83 should be of a minimum thickness to allow sheath 36 to be properly placed at the desired tissue access site before being completely dissolved.

The inner core 84 of sheath 36 may have the same or a different material than outer coating 83. Inner core 84 is made of absorbable materials. The material may be bioabsorbable, non-bioabsorbable or semi-bioabsorbable. The material of inner core 84 may be composed of collagen, gelatin, cellulose, absorbable polymers and combinations thereof. Prior to being inserted into the body, the material of inner core 84 is typically compressed (i.e., by outer coating 83) to enhance the volume of body fluids which can be absorbed. The material of inner core 84 also has the property of expanding in volume when absorbing body fluids. Inner core material is preferably a less rigid material than outer coating 83 so that the inner core material can easily deform about the tissue access site during insertion. Collagen is a soft, highly absorbable material which is preferred for inner core 84.

With reference to the generic description of the invention illustrated in FIGS. 3, 4, and 5, outer coating 83 permits sheath 36 to be easily moved to the tissue access site without damaging subcutaneous tissue 61 while body fluids permit collagen in inner core 84 to radially expand to occlude the longitudinally-extending central opening 89 of sheath 36 thus blocking or sealing the tissue access site at membrane 63. Further, as outer coating 83 dissolves, inner core 89 expands not only radially inwardly, but also radially outwardly to further compress subcutaneous tissue 61 and minimize bleeding. Again, the thickness of coating 83 is predetermined such that occlusion of central opening 89 substantially occurs to seal the tissue access site before the radially-outwardly expansion and subsequent tissue compression occurs and the outside diameter of sheath 36 is suitably sized to achieve a sufficient level of subcutaneous tissue compression upon initial injection to minimize bleeding.

Sheath 36 can be inserted on tubular medical device 70 prior to being inserted into the patient or prior to tubular medical device 70 being removed from the patient. When sheath 36 is positioned about tubular medical device 70 prior to treatment, damage to sheath 36 may occur if precautions are not taken. One source of damage to sheath 36 is in the form of contamination. In a medical environment, there exists many infectious micro-organisms. During an angiogram or other medical treatment, sheath 36 is exposed to these foreign micro-organisms prior to being inserted into the patient. The longer the particular medical treatment, the more likely sheath 36 may be contaminated. Sheath 36 may also become deformed during the medical treatment. As noted, sheath 36 is preferably formed of a bioabsorbable material. One such bioabsorbable material is gelatin. Gelatin has the special property of becoming slippery when body fluids such as blood contacts the gelatin surface. When the gelatin and body fluids interact, the gelatin is dissolved forming a slippery surface. During a long and/or complicated medical treatment, body fluids may come in contact with and completely dissolve the gelatin. When the time comes for in situ application of sheath 36, the slippery surface has dissolved and application becomes difficult. In addition, sheath 36 is comprised of absorbable materials, which absorb body fluids. As the body fluids are absorbed into sheath 36, such materials typically expand. If too much body fluid is absorbed into sheath 36, sheath 36 will deform due to expansion, thus preventing sheath 36 from being inserted through skin surface 60 and/or damaging the surrounding subcutaneous tissue 61 during insertion. The expanded sheath 36 may also stick to tubular medical device 70 and may be damaged due to friction and/or shearing from being slid along tubular medical device 70 during insertion.

Damage to sheath 36 can be avoided by hermetically sealing sheath 36 with a substance, such as plastic, which protects sheath 36 from contamination and contact with body fluids. Prior to inserting sheath 36 into the tissue access site, the seal about sheath 36 is removed. Preferably, sheath 36 is designed such that it can be quickly and easily inserted about tubular medical device 70 just prior to the time sheath 36 is to be inserted into the tissue access site. One such design is illustrated for sheath 36a in FIG. 6. Sheath 36a is generally of a cylindrical shape with a slit 90 extending, longitudinally from proximal end to distal end 81 and radially through the wall of sheath 36a from outside diameter to inside diameter. Prior to sheath 36a being inserted about tubular medical device 70, slit 90 is opened and sheatt 36a inserted about the circumference of tubular medical device 70. Slit 90 is preferably spread open only enough so as to be fitted about tubular medical device 70. Otherwise, sheath 36a may be creased and/or torn on the side opposite slit 90. Once sheath 36a is inserted about tubular medical device 70, slit 90 is closed. Preferably, the inside cylindrical surface of sheath 36a is formed such that once slit 90 is closed, the inside cylindrical surface of sheath 36a closely conforms to the outer surface of tubular medical device 70. Preferably, at least one of the longitudinally-extruding edges 91, 92 forming slit 90 has a sticky surface maintaining slit 90 closed after sheath 36a is applied to tubular medical device 70. The sticky surface which could be mechanically formed such as like a "velcro" surface tends to "glue" the surfaces together. Conceptually, sheath 36a could be made of two cylindrical halves simply applied as a hollow cylinder to tubular medical device 70.

Figure 7:
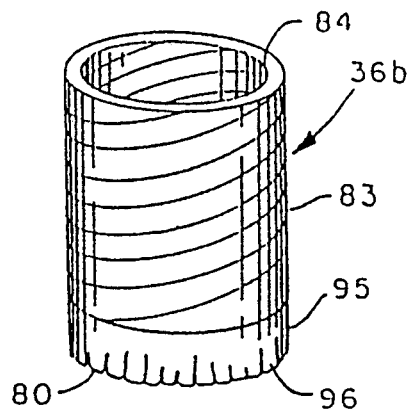
FIG. 7 is a schematic, perspective view of a modified form which the sheath of my invention can take.

FIG. 7 illustrates another form of sheath 36, which is designated by reference numeral 36b and which is particularly applicable for sheath application as a vascular plug. Sheath 36b is essentially constructed as described above with a rigid outer coating 83 and a soft inner core 84. However, sheath 36b has a distal portion 95 extending from its distal end 80, which preferably is fretted as at 96. Distal position is composed of a soft sticky substance such as a soft collagen. A very thin bioabsorbable coating may be applied to distal position 95 just sufficient to permit sheath 36b to be inserted to the blood vessel site.

Figure 8:
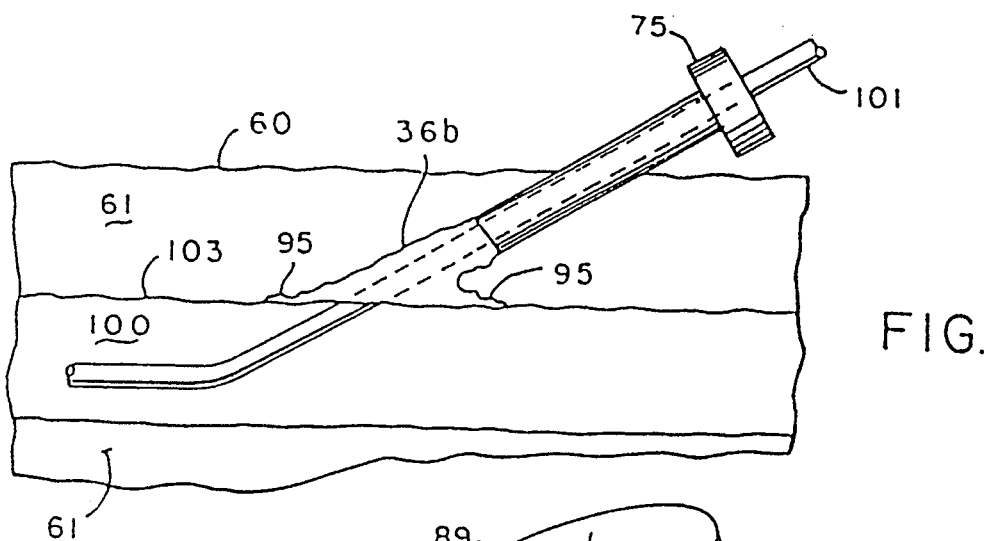
FIG. 8 is a schematic, elevation view of the access site of the patient showing deformation of the sheath of FIG. 7 when applied to plug a blood vessel.
Figure 9:
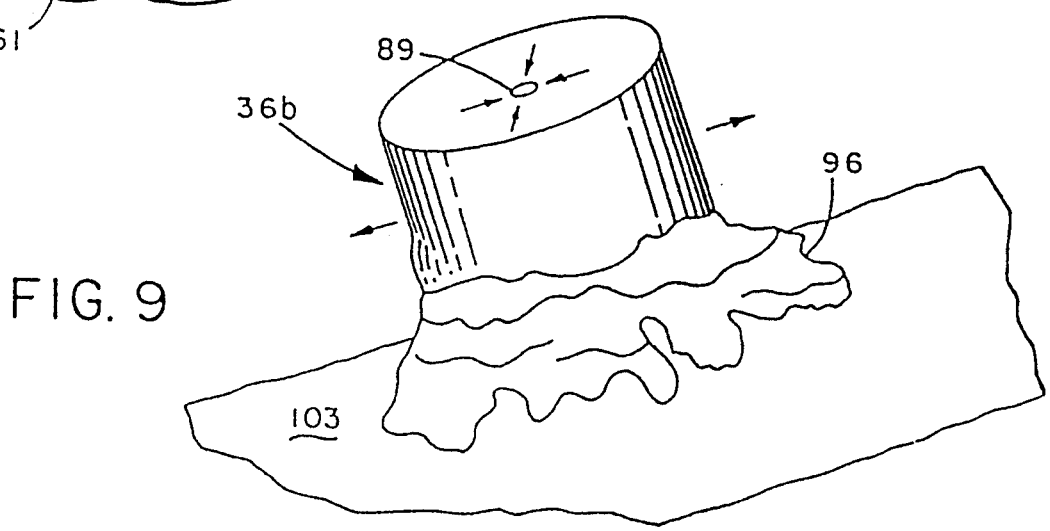
FIG. 9 is a schematic perspective view of the sheath of FIG. 7 in its plugged configuration after removal of the tubular medical device and pusher mechanism shown in FIG. 6.

Application of sheath 36b as a vascular plug may be explained by reference to FIGS. 8 and 9 relative to any conventional vascular treatment such as an angiogram. Those skilled in the art readily know that an angiogram is a treatment for removing deposits which have accumulated along the inner wall of an artery 100 (i.e., blood vessel). The procedure typically employed user a conventional needle stick to locate an artery 100, the stick penetrating the subcutaneous tissue 61 and providing the tissue access opening to artery 100. A conventional guide wire is then fed through the needle into the artery, and the needle is removed with the guide wire left in place. Next, a conventional introducer sheath 101 having a tissue dilator at its distal end with a valve and a pressure/sample port at its proximal end (not shown) is fed over the guide wire so that introducer sheath 101 extends into artery 100. A conventional catheter is then fed over the guide wire and the angiogram procedure performed after which the catheter and guide wire are removed. All of these steps are conventional and are not shown in the drawings. Sheath 36b is then placed on introducer 101 and, depending on the configuration of introducer 101, sheath 36b may or may not have slit 90. Also, positioned on introducer 101 is pusher mechanism 75. Pusher mechanism 75 is use to push sheath 36b against the blood vessel wall 103 (.i.e., artery) and because distal portion 96 is soft, it conforms to the shape of vessel wall 103 as best shown in FIG. 9. Sheath 36b is held in place by pusher 75 as the introducer sheath 101 is withdrawn and while sheath 36b is being held in this position, the collagen swells and expands radially-inwardly as discussed above to occlude central passage 89 and thus plug the tissue access opening (i.e., the opening caused in artery 100 ) to perform the angiogram. Sheath 36b also expands radially-outwardly as discussed above, wedging itself further into subcutaneous tissue 61 to firmly seal or maintain sheath 36b, now a plug, in its in situ place or position while also minimizing bleeding from subcutaneous tissue 61. In summary of this embodiment of the invention, the soft distal portion 95 of sheath 36b spreads about the access site to seal seepage from the site while the radially-inward expansion of the non-bioabsorbable collagen plugs central opening 89 preventing escape of body fluids and the radially-outward expansion of the collagen further wedges sheath 36b into subcutaneous tissue 61 to maintain sheath 36b in its in situ position to prevent loss of body fluid thus forming an effective vascular plug.

The invention has been described with reference to a preferred embodiment and alternatives thereof. It is believed that many modifications and alterations to the embodiments discussed herein will readily suggest themselves to those skilled in the art upon reading and understanding the detailed description of the invention, It is intended to include all such modifications and alterations insofar as they come within the scope of the present invention, Having thus defined the invention, it is claimed:

1. A medical device for use in a human patient to minimize bleeding comprising:

an elongated member extending along a path to a site within said patient whereat bleeding is likely to occur;

a hemostatic sheath having a central, longitudinally extending passageway receiving, generally concentrically, said elongated member and slidably disposed about said elongated member; and means for causing relative sliding motion between said sheath and said elongated member for depositing said sheath at said site whereby fluid at said site causes swelling of said hemostatic sheath along its interior and exterior surfaces to prevent bleeding from said site.

2. The medical device of claim 1 wherein said elongated member is tubular and further including means activated by said relative movement of said sheath and said tubular member for positively positioning said sheath at said site.

3. The medical device of claim 2 wherein said positioning means includes means for detecting sensatory vibration of said tubular member when and as said sheath is positioned at said site.

4. In a surgical procedure that employs insertion of a needle-form instrument through the skin and along a path to a deeper lying site, the puncture at said site creating a risk of hemorrhage, the step of completing the procedure comprising providing a hemostatic element comprised of hemostatic material, said element having an internal passage and being provided concentrically about an elongated member that extends along said path to said site, locating said hemostatic element at said site by locating it concentrically over said elongated member and causing relative sliding motion between the hemostatic element and said elongated member, blood from said site thereafter causing swelling of hemostatic material along the interior passage of said hemostatic element as well as hemostatic material along the exterior of said hemostatic element to prevent hemorrhage.

5. In a surgical procedure that employs insertion of a needle-form instrument through the skin and along a path to a deeper lying site, the puncture at said site creating a risk of hemorrhage, the step of completing the procedure comprising providing a hemostatic element comprised of hemostatic material and, with a removable device that has a side formation for detecting a tissue transition at said site, detecting a tissue transition, and on the basis of said detection, locating said hemostatic element at said site and then removing said removable device from said site.

6. The surgical procedure of claim 5 comprising providing an elongated member along the path to said site, guiding said removable locating device to said site along said elongated member, and after removing said locating member, removing said elongated member from said path.

7. The surgical procedure of any one of claims 4, 5 or 6 wherein the cross-sectional diameter of said hemostatic element is larger than the cross-sectional diameter of said elongated member.

8. The surgical procedure of any one of claims 4, 5 or 6 wherein the cross-sectional diameter of said hemostatic element is selected to be larger than the cross-sectional diameter of said puncture.

9. The surgical procedure of claim 8 wherein the portion of said hemostatic element that forms its exterior is in a hard state, during insertion, and has a surface of low coefficient of friction.

10. The surgical procedure of claim 9 wherein, during insertion, interior portions of said hemostatic element are soft relative to the exterior of said element.

11. The surgical procedure of any one of claims 4, 5 or 6 comprising blindly locating said hemostatic element by detecting a tissue transition at said site.

12. The surgical procedure of claim 11 wherein detecting of said tissue transition is effected by a device extending along said path to said site.

13. The surgical procedure of claim 12 wherein said device is elongated and has a side formation for detecting said tissue transition.

14. The surgical procedure of claim 13 comprising detecting said tissue transition by movement of said device.

15. The surgical procedure of claim 14 comprising detecting said tissue transition by a sensation that is produced at said side formation and felt by the user.

16. A system for treating the risk of hemorrhage from a puncture caused by a surgical procedure that employs insertion of a needle-form instrument through the skin and along a path to a deeper lying site, comprising:
   an elongated medical device for accessing the tissue to said deeper lying site,
   a hemostatic element comprised of hemostatic material constructed to be slid along exterior surfaces of said elongated medical device, and
   a locator device adapted to be removable from said site and constructed to be extendable along said path and having a side formation for detecting a tissue transition at said site and, on the basis of said detection, locating said hemostatic element at said site and then removing said device from said site.

17. The system of claim 16 wherein said hemostatic element has a hard outer surface.

18. The system of claim 16 wherein the cross-sectional diameter of said hemostatic element is larger than the cross-sectional diameter of said elongated member.

19. The system of claim 16 wherein said side formation is a feeler formation that detects said tissue transition by causing a sensation that is felt by the user.

20. A hemostatic sheath element for use with a medical device accessing a site of a body within a human patient, a locator device for detecting a tissue transition at said site, said sheath element adapted to be inserted where said body has been accessed to minimize bleeding by locating it over exterior surfaces of said medical device and causing relative sliding motion between said sheath element and said medical device, blood from said site thereafter causing said sheath element to swell in the region previously occupied by said medical device to prevent hemorrhage, said locator device and hemostatic element are constructed such that the hemostatic element is pushed along the elongated medical device by said device.

21. The system of claim 20 wherein the hemostatic element and locator device are disposed concentrically over said medical device.

22. The system of claim 21 wherein the locator device releasably carries said hemostatic material at its distal end.

23. In a surgical procedure that employs insertion of a needle-form instrument through the skin and along a path to a deeper lying site, the puncture at said site creating a risk of hemorrhage, the step of completing the procedure comprising providing a hemostatic element comprised of hemostatic material, said element having its exterior constructed to directly, slidably engage tissue bounding said path, locating said hemostatic element at said site by pushing said element to slide along an elongated member disposed in said path as the exterior of said element slidably engages said tissue bounding said path, withdrawing said elongated member, blood from said site thereafter causing said hemostatic element to swell in the region previously occupied by said elongated member to prevent hemorrhage, the cross-sectional diameter of said hemostatic element being selected to be larger than the cross-sectional diameter of said puncture, the portion of said hemostatic element that forms its exterior being in a hard state, during insertion, and having a surface of low coefficient of friction, wherein during insertion, interior portions of said hemostatic element are soft relative to the exterior of said element.

24. In a surgical procedure that employs insertion of a needle-form instrument through the skin and along a path to a deeper lying site, the puncture at said site creating a risk of hemorrhage, the step of completing the procedure comprising providing a hemostatic element comprised of hemostatic material, said element having its exterior constructed to directly, slidably engage tissue bounding said path, blindly locating said hemostatic element at said site by detecting a tissue transition at said site, and pushing said element to slide along an elongated member disposed in said path as the exterior of said element slidably engages said tissue bounding said path, withdrawing said elongated member, blood from said site thereafter causing said hemostatic element to swell in the region previously occupied by said elongated member to prevent hemorrhage.

25. The method of claim 24 wherein detecting of said tissue transition is effected by a device extending along said path to said site.

26. The method of claim 25 wherein said device is elongated and has a side formation for detecting said tissue transition.

27. The method of claim 26 comprising detecting said tissue transition by movement of said device.

28. The method of claim 27 comprising detecting said tissue transition by a sensation that is produced at said side formation and felt by the user.

* * * * *